United States Patent
Trovato et al.

(10) Patent No.: US 9,747,684 B2
(45) Date of Patent: *Aug. 29, 2017

(54) RF ABLATION PLANNER

(75) Inventors: Karen I. Trovato, Putnam Valley, NY (US); Douglas Summers-Stay, Bellbrook, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1051 days.

This patent is subject to a terminal disclaimer.

(21) Appl. No.: 12/523,163

(22) PCT Filed: Jan. 10, 2008

(86) PCT No.: PCT/IB2008/050087
§ 371 (c)(1),
(2), (4) Date: Jul. 15, 2009

(87) PCT Pub. No.: WO2008/090484
PCT Pub. Date: Jul. 31, 2008

(65) Prior Publication Data
US 2010/0063496 A1   Mar. 11, 2010

Related U.S. Application Data

(60) Provisional application No. 60/886,421, filed on Jan. 24, 2007.

(51) Int. Cl.
*A61B 18/12* (2006.01)
*G06T 7/00* (2017.01)
(Continued)

(52) U.S. Cl.
CPC ............ *G06T 7/0012* (2013.01); *A61B 90/36* (2016.02); *A61B 34/10* (2016.02); *A61B 34/20* (2016.02);
(Continued)

(58) Field of Classification Search
CPC .................... A61B 2034/107; A61B 34/20
(Continued)

(56) References Cited

U.S. PATENT DOCUMENTS 6,139,544 A * 10/2000 Mikus et al. ............... 606/21
6,241,725 B1 * 6/2001 Cosman ...................... 606/41
(Continued)

FOREIGN PATENT DOCUMENTS

EP   1791070 A2   5/2007

OTHER PUBLICATIONS

Kalkofen, D., et al.; Integrated Surgical Workflow for Augmented Reality Applications; 2006; http://mustang.icg.tu-graz.ac.at/publ/ami-.

(Continued)

*Primary Examiner* — Thomas Giuliani (57) ABSTRACT

In planning an ablation procedure, a planned target volume (PTV) is imported, which is typically selected by a doctor but may be computer identified. An initial set of candidate ablation regions that covers the PTV is computed. Ablation probe trajectories that avoid critical structures are computed to provide surgical 5 options for safe entry points and angles. An optimization component determines a minimum number of ablation regions, which fully covers the PTV, and generates locations and orientations for each ablation. A tracking system can be given these ablation targets, enabling the surgeon to control the probe more precisely to the desired location.

30 Claims, 9 Drawing Sheets

(51) Int. Cl.
  *A61B 90/00* (2016.01)
  *A61B 34/10* (2016.01)
  *A61B 34/20* (2016.01)
(52) U.S. Cl.
  CPC ... *A61B 2034/104* (2016.02); *A61B 2034/107* (2016.02); *G06T 2207/30004* (2013.01)
(58) Field of Classification Search
  USPC ............... 606/32; 607/98, 99, 115; 128/922
  See application file for complete search history.

(56) References Cited

U.S. PATENT DOCUMENTS

| | | | |
|---|---|---|---|
| 6,575,969 | B1 | 6/2003 | Rittman, III et al. |
| 8,267,927 | B2* | 9/2012 | Dalal ................. A61B 18/1477 606/34 |
| 2003/0171672 | A1 | 9/2003 | Varghese et al. |
| 2003/0212394 | A1* | 11/2003 | Pearson ............. A61B 18/1477 606/41 |
| 2004/0220562 | A1 | 11/2004 | Garabedian et al. |
| 2005/0041843 | A1* | 2/2005 | Sawyer ........................ 382/128 |
| 2006/0089624 | A1 | 4/2006 | Voegele et al. |
| 2011/0015628 | A1* | 1/2011 | Dalal et al. ..................... 606/34 |

OTHER PUBLICATIONS

Wood, B. J., et al.; Technologies for guidance of Radiofrequency Ablation in the Multimodality Interventional suite of the Future; 2007; Journal of Vascular and Interventional Radiology; 18(1)9-24.
Perlin, K., et al.; Hypertexture; 1989; Computer Graphics; 23(3)253-261.

* cited by examiner

RF ABLATION PLANNER

CROSS REFERENCE TO RELATED APPLICATIONS

This application claims the benefit of U.S. provisional application Ser. No. 60/886,421 filed Jan. 24, 2007, and PCT application serial no. PCT/IB2008/050087 filed Jan. 10, 2008, both of which are incorporated herein by reference.

The present application relates to radio frequency ablation (RFA), particularly involving inserting an RF electrode "probe" into a patient such that an expected ablation zone covers and kills the tumor by raising its temperature. However, it will be appreciated that the described technique may also find application in other ablation techniques, other surgical techniques or other radiation therapy techniques.

A probe may be connected to power for a predetermined time period (e.g., approximately 15 minutes, or some other suitable time period), and ablates in a variety of shapes, but commonly a sphere or ellipsoid. Currently, a surgeon may make a mental note about a location of a lesion to be ablated and may insert the probe utilizing various types of image guidance. Because probes are very expensive, a surgeon is deterred from using multiple probe sizes or configurations, in favor of attempting to ablate a tissue mass using a minimum number of probes.

When a tumor or lesion exceeds a size that cannot be successfully covered by a single ablation, treatment success rate drops dramatically. A margin around the tumor, often 1 cm, may be considered necessary in order to kill microscopic cancer cells. Leaving any portion of the tumor untreated can result in a recurrence, often an aggressive recurrence. Moreover, determining coverage of the tumor involves complex 3D geometric calculations and visualization which can be difficult for even the best of surgeons. Still furthermore, each additional ablation adds to surgical and anesthesia time and cost and increases risk to the patient.

Other difficulties that can arise relate to complicated mental visualization of a single target location in 3-space, and difficulty in controlling a probe so that it accurately reaches the target location, which adds additional potential for error. Additionally, ablation shapes often do not match the shape or size of the tumor, causing ablation of healthy tissue surrounding the tumor. The tumor may also be comprised of two or more smaller tumor regions that are not geometrically connected, but near enough to each other so that they should be treated together. Ablations may also damage 'critical regions' that can cause serious injury to the patient. Probe entry angles are typically chosen because they match the imaging system rather than because they minimize the number of ablations or reduce procedure risk. Furthermore, since each surgeon mentally creates a picture and plan, and manually directs the probe, there is no chance for repeatability, which is an important aspect of "evidence based medicine." The present application provides new and improved tumor ablation systems and methods, which overcome the above-referenced problems and others.

In accordance with one aspect, a system for planning an ablation procedure for ablation of a tissue mass in a patient includes a representation of the target mass. The target volume includes the tumor and any optional margin. The representation can be an imported volume, such as a region segmented from a CT image. Alternatively, it may be specified by a user interface, where the user outlines boundaries, using drawing tools, from different views of image data, and the system computes the related 3D voxels. An optimization component receives image data related to the mass and determines the ablation regions to cover the mass. The regions may be selected so that they minimize the number of ablations (and thus procedure time), or the regions may be selected to minimize the damage to healthy tissue adjacent to the target volume.

In another aspect, critical regions are identified so that the planning avoids them.

In another aspect, a subset of a target volume that is difficult to reach is identified because of the relative position to a critical region. This subset may be used to suggest that the surgeon consider separating the target from the critical region, such as by saline injection.

In another aspect, the set of potential entry points and orientations may be identified that avoid forbidden regions. The advantage is that it narrows the set of orientations and entry vectors to only those that are feasible. This enables the system to offer the surgeon a selection of feasible entries. The number of ablations and collateral damage can be provided for each entry, or only the best of the feasible entries can be suggested.

One advantage is that critical regions (e.g., bone, bowel or the like) that are within an ablation region may be identified, and actions may be taken to avoid ablation thereof.

Another advantage resides in minimizing surgery duration.

Another advantage resides in accurately matching the ablation volume to the target.

Another advantage is that specific, quantitative target locations and orientations are determined. These specific values can be used to guide the surgeon with tracking devices, such as magnetic trackers. They may also be used to control other devices such as robots, which require quantitative data.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating various aspects and are not to be construed as limiting the invention.

FIGS. 4A, B, C, and D illustrate graphical representations of various actions associated with ablation planning.

Ablation devices, such as an elongated slender probe, are typically inserted into a tumor, lesion, or other tissue to be ablated, and the probe tip is heated using a high radio frequency in order to heat the surrounding tissue to a temperature sufficient to kill cells therein, often considered as 50 degrees Celsius. Although the present application primarily describes radio frequency (RF) ablation techniques, which can be used in many locations, including liver, kidney, breast, lung and others, it will be understood that cryoablation, microwave, and other ablation and treatment procedures can be planned similarly.

An ablation zone is typically, located relative to the probe tip and is spheroid or ellipsoid in shape, noting that a sphere is an ellipsoid with equal a,b,c axes. When a tumor is larger than the ablation region for a given probe size, a surgeon selects more than one probe position to generate a plurality of ablated regions that overlap to cover the entire tumor mass. A typical ablation process involves defining the target region, inserting the probe to the desired location, and applying power to the probe for about 15 minutes, causing the probe tip to heat.

A planned target volume (PTV) is defined that envelopes the entire tumor mass as well as a buffer region (e.g., typically one centimeter or so) around the tumor. This ensures ablation of all tumor cells and microscopic tumor cells, found in the buffer zone, in order to mitigate a recurrence of the tumor.

In accordance with various features presented herein, probe position is selected by determining potential trajectories along which the tumor mass is reached by a probe without passing through critical regions or bone tissue. One or more trajectories are then selected by a surgeon or automatically to optimize a number of ablations performed to ablate the entire tumor mass.

A series of ellipsoid volumes is defined to encompass the PTV. As described in detail below, a computer-based optimization technique covers the PTV, based on the size of the ellipsoids. Additionally, the ellipsoids are moved to minimize the amount of ellipsoid ablation zone that extends into healthy tissue beyond the PTV while still covering the entire PTV. Redundant ellipsoids may be discovered as the ellipsoids are moved, and can be removed to reduce the number of ablations required to ablate the PTV. Moreover, the technique can be iterative to minimize the number of ellipses used to fill the PTV space, and thereby minimize the number of ablations performed. The optimization can be performed for several or all potential trajectories for probe insertion to identify the insertion angle(s) that minimize the number of ablations required or reduce the collateral damage of healthy tissue. Additionally, the technique can ensure that a planned ablation ellipsoid volume does not intersect a critical region, such bone or other sensitive tissue.

Figure 1:
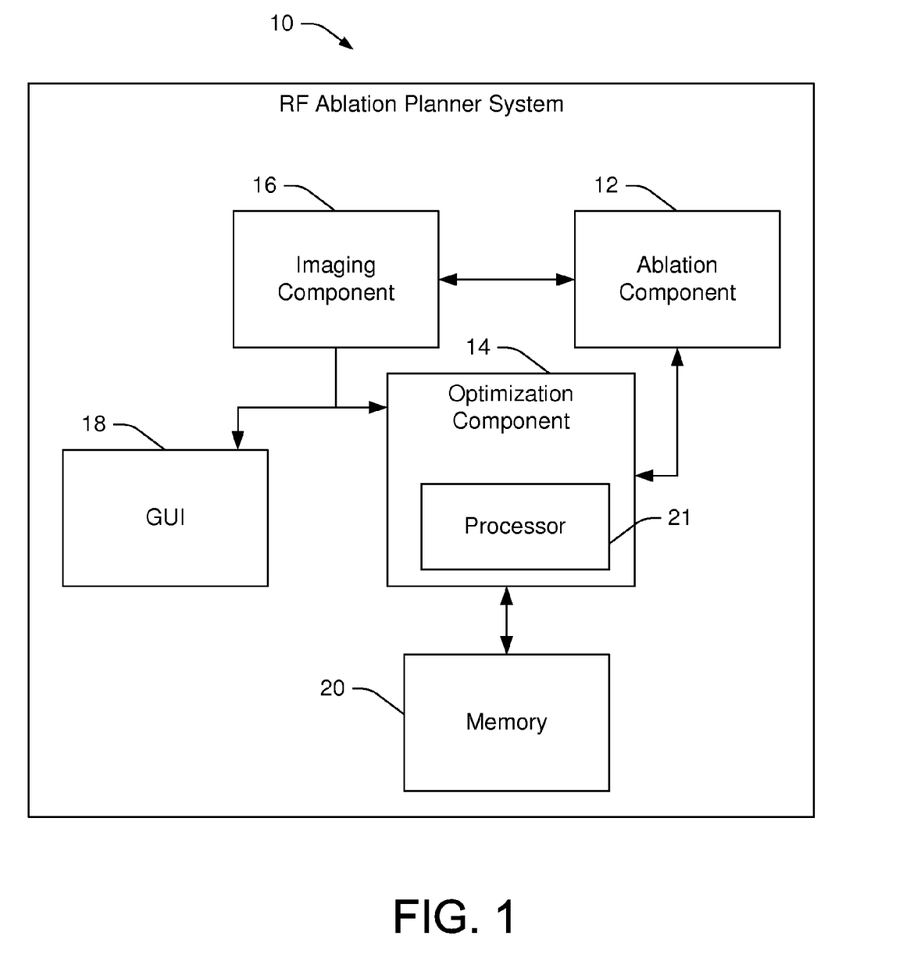
FIG. 1 illustrates a radio frequency (RF) ablation planner system that facilitates generating a plan for performing one or more ablation protocols to treat a tumor mass or lesion in a patient, in accordance with one or more aspects set forth herein.

FIG. 1 illustrates a radio frequency (RF) ablation system 10 that facilitates generating a plan for performing one or more ablation protocols to treat a tumor mass or lesion in a patient. Successful treatment of large tumors can be achieved by planning ablation probe positions precisely so that no part of the tumor is left untreated and accurately executing the plan. The system 10 generates a quantitative ablation plan, including target positions and orientations for each ablation. It may optionally identify the entry point or points on the outside of the body that lead to the target(s). The ablation plan ensures that all areas of the tumor are covered, and reports the number of ablations required for complete ablation using a particular probe. The system 10 also utilizes optimization techniques to minimize the number of ablations. Since the plan is quantitative, it can be carried out using a robot and/or by using registered image guidance, such as by quantitatively tracking the ablation probe.

The system 10 includes an ablation component 12 that is operatively connected to each of an optimization component 14 and an imaging component 16, such as a CT scanner. The system 10 can additionally or alternatively include an ultrasound imaging component, an X-ray fluoroscopy imaging component, a magnetic resonance imaging system, a picture archiving and communication systems (PACS) or any other suitable imaging component or delivery system. The ablation component 12 in one embodiment is an RF ablation system, which includes a power source, a radio frequency generator, a probe operatively coupled thereto, etc., as well as any other suitable component to facilitate inserting the probe into a tumor mass and heating the tumor mass to a temperature sufficient to kill tumor cells (e.g., approximately 50 degrees Celsius) within a region relative to the probe tip. The ablation component 12 in an alternative embodiment includes a high-intensity focused ultrasound component (HIFU), which ablates tissue in a particular region through the use of mechanical vibration and/or heating properties of ultrasound. In some systems, an ultrasound ablation region can be predicted, even if the ultrasound is not strictly 'focused', using an array of transducer elements. The imaging component 16 generates data which is reconstructed into a 3-D image. Objects such as a lesion, organs, critical regions can be segmented automatically using algorithms or by hand with drawing tools along each of the axes. The segmentation produces a description of the volumetric regions associated with the specific objects. In particular, a volume may be optionally presented to a user via a graphical user interface 18 (GUI). The volume may be 'grown' by a desired distance so that the tumor plus margin are included in the resulting volume. Whenever the word 'tumor' is used herein, particularly regarding optimization, it is assumed to mean the 'Planned Target Volume' (PTV), which covers the specified tumor plus margin that together are intended for full coverage. Systems such as Pinnacle provide capabilities to either manually or semi-automatically segment objects from medical images. Pinnacle also enables the user to set a margin, whereupon a new volume (the PTV) is defined. The optimization component 14 analyzes information associated with the PTV, particularly the dimensions, and for a given ablation probe defines a set of ablation positions with orientations. In one example, the optimization component 14 identifies the fewest number of ablations possible that cover the PTV. In another example, the optimization component 14 identifies the ablation positions with orientations that spares the most healthy tissue (i.e. minimizes collateral damage). In another example, additional object volumes are segmented that denote 'critical regions' of tissue or bone that are not to be ablated, and the optimization component 14 attempts to generate either the fewest ablations or minimize collateral damage, while also avoiding these regions. In some cases however, the optimization component 14 produces unablated areas, whereupon the user is alerted and the regions can be displayed on the User Interface. Information associated with ablation techniques, ablation periods, probe size, temperature, PTV, ellipsoid volume, ellipsoid centers, PTV reductions and/or adjustments, protocols for minimizing PTV, probe entry angles and/or positions, and any other suitable information related to system performance is stored in a memory 20, which is also operatively coupled to the optimization component 14. Additionally, optimization component 14 includes a processor 21 for performing various analytical actions, executing one or more routines, and the like. For example, the processor 21 can and can execute routines such as those described with regard to FIGS. 2, 5, and 10. According to some aspects, the optimization component comprises a computer that includes one or more processors and memory that stores information related to ablation techniques.

The probe entry angles may be selected by the doctor and entered manually or graphically via the user interface. Alternatively, the system 10 can facilitate the selection of probe entry angles that avoid "critical regions," as the probe travels through the body to the tumor. In theory, critical regions that should be protected from ablation may be different from other critical regions that can be punctured by the probe entry path. In RF ablation, the current probes require a physical path between the skin and target. In other ablation techniques however, such as HIFU, the target may be reached without disturbing the intervening tissue. However in practice, critical regions for ablation and entry path are often the same. The optimization component 14 selects ablation volumes that do not intersect a critical region. In some cases, a critical region may be so close to the tumor that it cannot be easily accessed. In this situation, the critical region is highlighted to alert a user that additional preparation procedures are desirable or recommended, such as injection of saline to separate or thermally insulate the tumor from the critical region.

The selection of probe entry points (optional) and ablation points (e.g., placement of the probe tip with a given offset for the expected ablation shape) is performed by the optimization component 14. According to other aspects, the optimization component 14 provides a plurality of suggested entry points and/or ablation points, which are presented to a user via GUI 18 for selection. In this manner, the RF ablation planner system 10 facilitates successful treatment of large tumors through planning the ablation positions precisely so that no part of the tumor is left untreated, no critical tissue is damaged, the plan generates quantitative goals enabling the ablation component 12 to use tracking or control to improve accuracy, and an overall system with more repeatable procedures.

According to other embodiments, a PTV for a tumor mass is pre-generated and stored, and is imported to the optimization component 14 at a later time for ablation procedure planning. The imported PTV is a three-dimensional representation of the PTV, which is generated using the imaging component 16, such as a CT scanner, an ultrasound imaging component, an X-ray fluoroscopy imaging component, a magnetic resonance imaging system, a picture archiving and communication systems (PACS) or any other suitable imaging component or delivery system. Once the PTV has been received, ablation volume centers are identified for one or more ablation volumes that completely envelop the PTV. The target ablation points (e.g., the centers) can be output to a tracking system, which may include a GUI, to assist a surgeon in probe placement along an intended insertion trajectory. Additionally or alternatively, the target ablation points may be output to the GUI 18 (e.g., with or without the tracking system) for approval and/or use by a surgeon when performing the ablation procedure.

Figure 2:
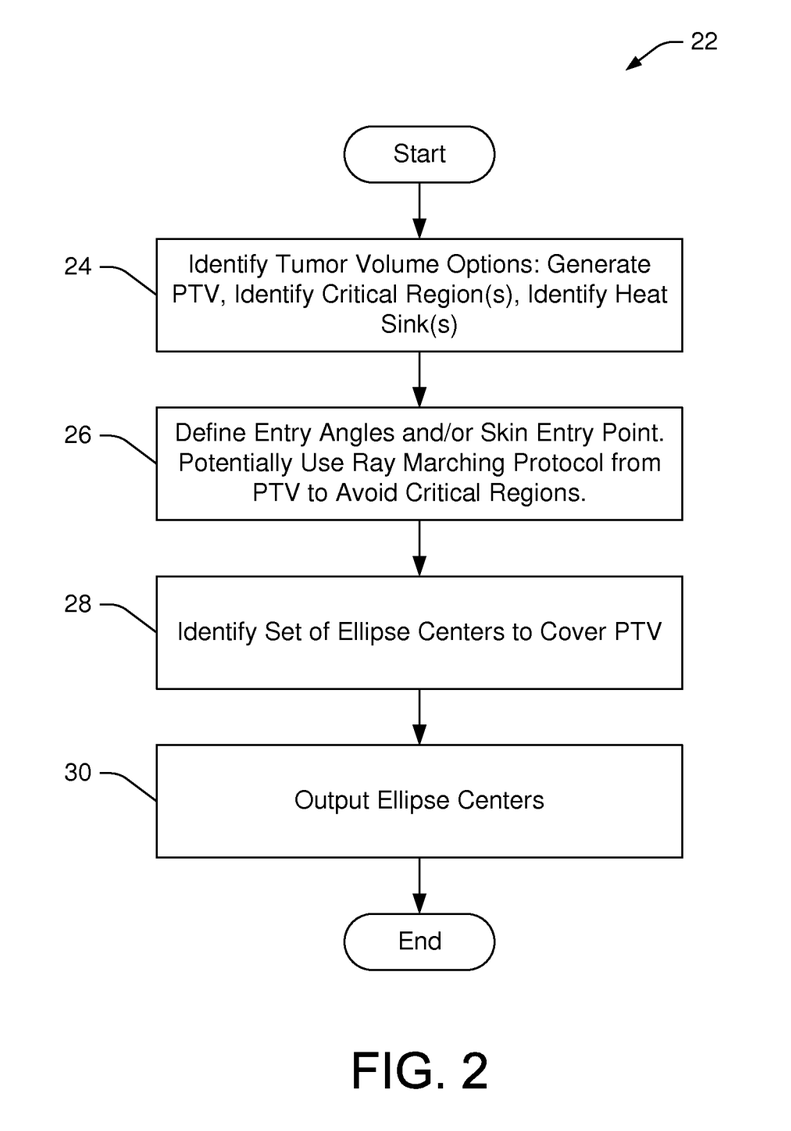
FIG. 2 illustrates an algorithmic method that generates a quantitative plan, including probe entry angles, for an ablation probe and a target position for each ablation.

FIG. 2 illustrates an algorithmic method 22 that generates a quantitative plan, including entry angles for an ablation probe and a target position for each ablation. The algorithm assures all tumor areas are covered and determines the ablations for complete tumor ablation using a particular probe. Additionally, the algorithm includes optimization techniques that minimize the number of ablations for a given tumor volume. In one example, the algorithm identifies a plurality of ablation ellipses that cover a planned target volume (PTV). The centers of the ellipses are pulled toward a centering "gravity point," which is located at the center of mass. Typically this falls within the PTV, however some unusual shapes, for example a 'C' shape, the point may actually be outside the PTV. As ellipses are pulled toward the gravity point, those ablation ellipsoids that do not cover a unique portion of the PTV are deleted to identify a minimal number of ablation ellipsoids and their respective centers. This occurs when enough ellipses are clustered so that an ellipse's critical coverage area is already covered by other ellipses. Once the ellipses are pulled together, the collateral damage is minimized.

Figure 3A:
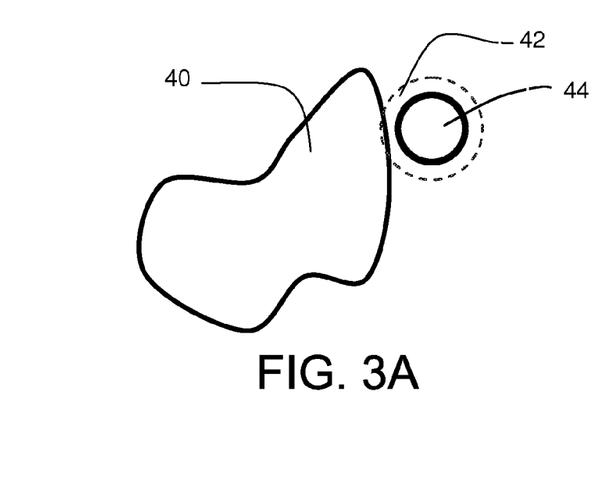
FIGS. 3A, B, and C show an example PTV near an aorta, and a graph of the resulting change in temperature as a function of the distance from the lumen of the aorta.

According to the method, at 24, a tumor volume is segmented and identified. The tumor can be any shape, and can be a collection of disconnected region. The PTV is then identified for ablation, e.g. the tumor volume plus an approximately centimeter-thick surrounding volume. FIG. 3, below, shows an example tumor that is grown by a fixed size in all dimensions. Although a circle is shown for this 2D example, a sphere can be used in the 3D example. Placing the center along the edge of the tumor forms a PTV boundary. This can be performed by other techniques as well. The best results can be obtained if disconnected regions are close together, ideally connected by the margin. If they are not connected, then it may be preferable to consider each cluster of margin-connected volumes as separate tumors for planning purposes. The PTV represents a volume with added margin around the tumor. Critical regions and heat sinks near the tumor are additionally identified at 24, typically by any of numerous segmentation techniques described in the literature and available in products. Each critical region, heat-sink, tumor, PTV, etc. is a region of interest (ROI). The machine segmentation can be automated, performed by manual outlining or a combination of both. Critical regions are organs or life-critical tissues that can be adversely affected by the heat. There are actually two types of critical regions. The first are those near the PTV, which should not be ablated. The second are those that are not to be punctured such as when an RF ablation probe enters the body. The bowel is a structure that should not be punctured or ablated. The primary affect is on workflow however. A surgeon may compute a set of ablations and then go to the extra work of segmenting only relevant (near PTV or near insertion path) critical structures to determine how they change the proposed procedure. For example, nerves that are near the proposed ablation area may be added afterward to see how the plan would have to change, and whether the procedure seriously risks those nerves. Other structures are segmented and identified as "heat sinks." For example, although it may seem that a critical structure such as the aorta should be protected from ablation, it actually protects itself because the blood flow is so rapid that it "self cools." The cooling causes problems however to nearby structures that require ablation, since the cooling competes with the heating process, resulting in an unablated area and risk of cancer relapse. In current RF ablation probes, the temperature after 15 minutes is higher near the probe than at the edges of the ablation region. Therefore it may be advisable to move the probe 3 mm closer to the aorta, so that the temperature near the surface of the aorta is closer to 55 degrees C. Computational fluid dynamics, based on the Navier-Stokes equations that describe liquid and gas flow, can be used to estimate the amount of heat that is lost due to proximity of a particular heat sink of a particular size and blood velocity.

At 26, entry angles and/or one or more entry points on a patient's skin are defined. In one embodiment, a ray marching protocol is employed to determine an entry point. The CT voxels are labeled as either 'free' or 'critical region', for example in a binary volume. A ray marching algorithm, such as the one introduced by Perlin (see, e.g.: K. Perlin and E. M. Hoffert, "Hypertexture", Computer Graphics, vol. 23, issue 3, pp. 253-261, 1989), is employed to identify locations on the skin that permit insertion of a probe into the PTV along a path that does not travel through a sensitive or critical region such as bones. Intuitively, this is similar to setting a light at the center of the tumor, having the critical regions (e.g., solid masses such as bone or the like) block the light, and identifying points where the light reaches the skin. A ray of light is "marched" from the center of mass (centroid) of the PTV in a linear 'ray' through the 3D image until one of three situations occurs:

1) The ray reaches the edge of the image volume, whereupon it restarts at a new orientation from the center of the PTV
2) The ray reaches the skin or another location approved as an entry point, whereupon the x,y,z location and ray orientation are be noted. This is a potential entry point, which may be shown graphically or stored in a list for selection or may be evaluated to determine the number of ablations required for coverage from this angle.
3) The ray reaches a voxel that is labeled 'critical region', whereupon a new ray is begun with a new orientation from the center of the PTV.

This procedure continues until all desired angles are evaluated. The choice of potential angles can be based on brute force discretization of orientations, random selection, narrowed by conventional protocol, or simply picked by the surgeon on the GUI. The ray marching procedure is analogous to the idea of placing a tiny light at the location of the PTV centroid, where critical regions block the light from reaching the skin for example. Lighted areas on the skin are therefore potential entry points and shadowed areas are not. The entry angle is important both clinically and computationally. The entry angle should be safe, avoiding critical regions, as described by this step. Clinically, it is preferred in the liver for example, to puncture the liver capsule only once, from one external location, and generate substantially parallel ablations to cover the PTV. This simultaneously reduces the computational complexity of the problem, since the coverage can be computed assuming a fixed orientation. Since ray marching is faster than the coverage analysis, pre-computing a subset of feasible entry points limits the number of coverage calculations.

At 28, a set of ellipse centers is defined, such that a plurality of 3-D ellipsoidal ablation volumes corresponding to respective ellipse centers collectively envelope the entire tumor mass. The ellipses have a geometry defined by standard a,b,c semi-axis values, satisfying $x^2/a+y^2/b+z^2/c=1$, translated to the identified centers and rotated by a given entry angle, such as is defined by 26. For example, a given ablation probe has a known ablation volume X based on it's a,b,c values and orientation. In one embodiment, Y ablations of the known volume X completely cover the PTV. Probe dimensions can be selected by a user (e.g., depending on the type of probe), and the system can optimize probe placement for the assigned or derived orientation. This method for determining ellipse centers also prevents the ablation of critical regions, and is described further in FIG. 5.

Figure 7:
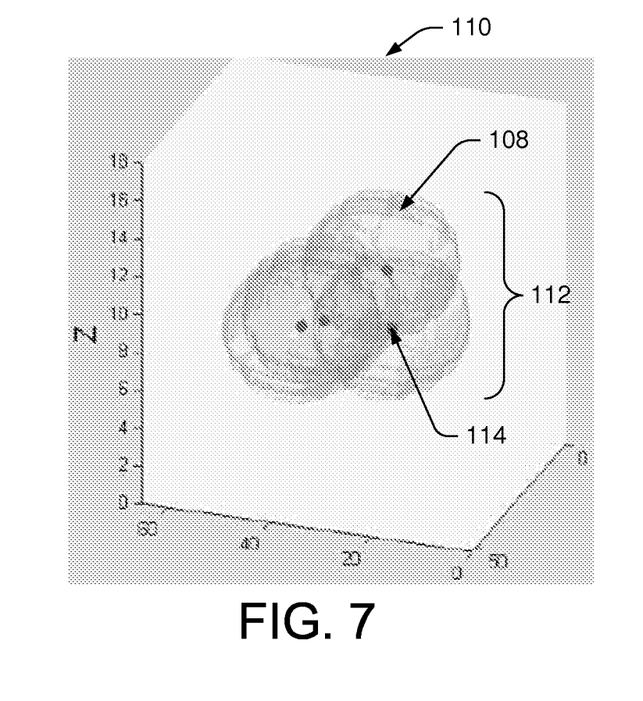
FIG. 7 illustrates an image of a plurality of ellipsoid ablation volumes.

At 30, the identified ellipse centers for the given probe size are output to a user, such as a surgeon or the like, via the graphical user interface such as is illustrated in FIG. 7, to permit the user to evaluate and/or execute the model. In this manner, the method 22 facilitates planning an ablation procedure to perform multiple ablations at different points, which in turn permits ablation of multiple ellipsoid volumes that overlap in space to ensure ablation of a non-uniformly-shaped tumor volume while avoiding regions in which ablation may be detrimental. A surgeon may also adjust the ellipses for factors not represented in the model. The ellipse centers along with the specified ablation probe geometry and orientation can be communicated to the ablation component 12. The ablation component 12 can then be used in conjunction with a tracking or robotic system. A tracking system provides visual feedback to the surgeon on the position and orientation of the tool, or tool-tip in real-time. The target can be displayed along with the live tracked location, often along with a registered patient image. Alternatively, a robot can be given the target point and can carry out the maneuver, with feedback from the tracking system and approval to proceed from the surgeon.

Figure 3B:
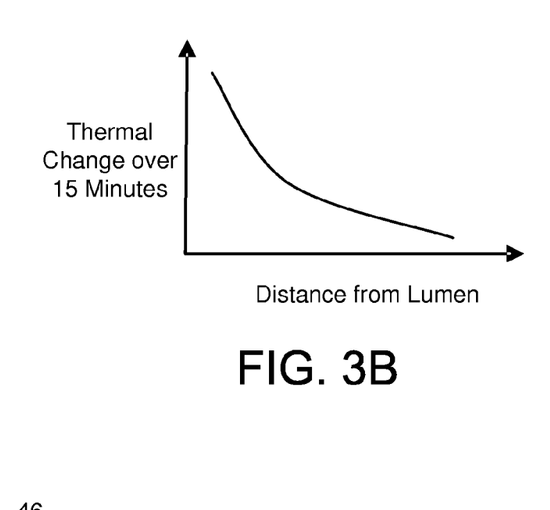
Figure 3C:
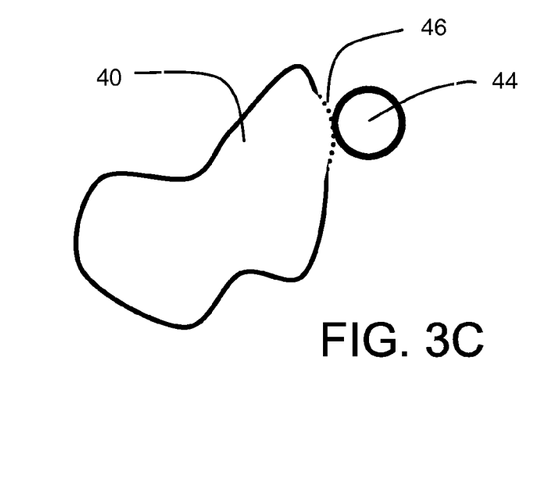

The ablation ellipses are placed so that they completely cover the PTV. The ellipses typically overlap, and may extend beyond the edges of the PTV. Once the routine 28 minimizes the number of ellipses their centers, i.e. the probe tip locations are other identifier of the probe locations is communicated visually to a surgeon, FIG. 3A shows an example PTV 40, near the aorta 44. In this case, the aorta has a thermal effect that tapers off to the distance shown as 42. The thermal change is the net result of the ability of the RF ablation probe to heat to at least 50 degrees Celsius and the aorta's cooling effect of 37 degrees Celsius over the ablation time. FIG. 3B shows a graph of the resulting change in temperature as a function of the distance from the lumen of the aorta. The lumen is the inner space of the vessel. The planner can partly account for such heat sink structures by ensuring that the PTV actually extends up to the heat-sink area to a distance corresponding to a higher expected temperature. In FIG. 3C, the PTV 40 is adapted so that it is moved closer to the aorta, causing a distension 46 of the PTV. This can also be accomplished by adding a compensating "virtual PTV" by hand, which extends the PTV in the direction of the aorta, in a location based on the expert opinion of the surgeon.

FIGS. 4A-D illustrate a plurality of graphical representations 60 of various actions associated with planning an ablation procedure for a patient with an otherwise inoperable tumor.

Figures 4A, 4B:
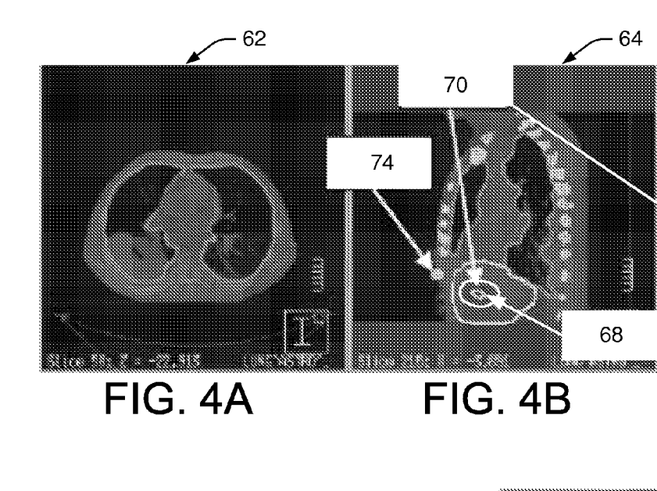
Figure 4C:
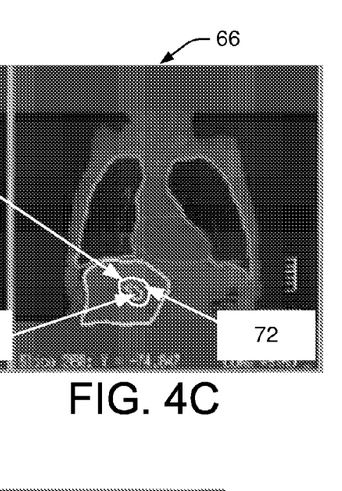
Figure 4D:
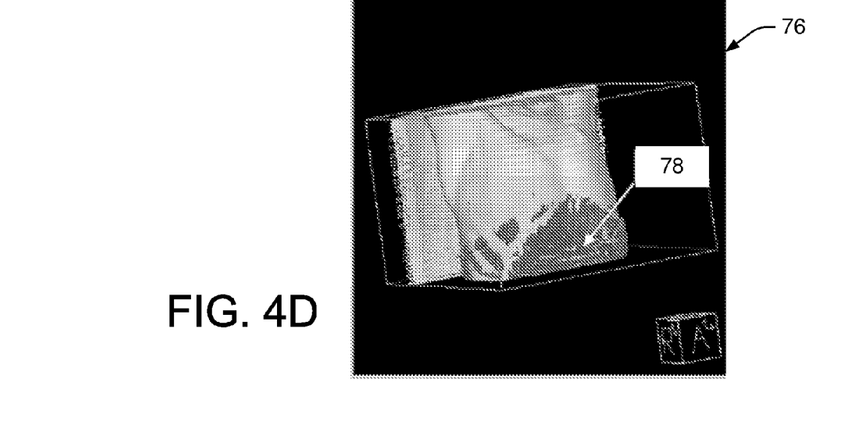

The graphical representations 60 include multiple views of a patient with an abdominal tumor, such as is generated using a magnetic resonance imaging tool or the like. In FIG. 4A, a CT image 62 illustrates an axial slice; image 64 shows a sagital view of the patient's thorax and upper abdomen; and image 66 illustrates a coronal view of the patient's thorax and upper abdomen.

A tumor mass volume 68 is segmented and enveloped by the planned target volume (PTV) 70, which is the visualized or otherwise calculated tumor mass 68 volume plus an additional safety margin, or buffer region 72, shown as the space between the tumor mass 68 and the perimeter of the PTV 70. The margin during surgery 72 is typically approximately 1 cm beyond the tumor, and can be verified by pathologists. A good surgical outcome is when the 'margins are clear', in other words, the outer edge of the surgically removed tumor is free from cancerous cells upon examination by a pathologist. When RF or other minimally invasive ablation techniques are used however, a pathologist is unable to assess the margins.

In essence, the margin attempts to compensate for different possible sources of error, but may be adjusted for particular patient anatomy and issues, such as if the treatment is palliative. Some of the sources of error include:

patient motion between the time of imaging and intervention, difficulty defining the precise edges of the tumor, inability to image microscopic cancers surrounding a tumor, difficulty quantifying target ablation positions that cover the tumor and minimize collateral damage, and difficulty carrying out the procedure to the specific targets.

The margin is defined by the surgeon, but is usually approximately 1 cm, but can be anywhere between 0 and approximately 1.5 cm. Reducing the error in any of these ways can reduce the margin.

A set of possible skin entry points 78 and an orientation angle for the ablation probe to the tumor 68 center is calculated by routine 26 of FIG. 2, or alternatively a position and orientation can be entered manually by a surgeon. A single entry point 74 is illustrated in FIG. 4B. The skin surface point that indicates successful (e.g., safe) travel from the skin to the tumor 68 is shown by the darkened (previously red) area at arrow 78 in image 76.

Figure 5:
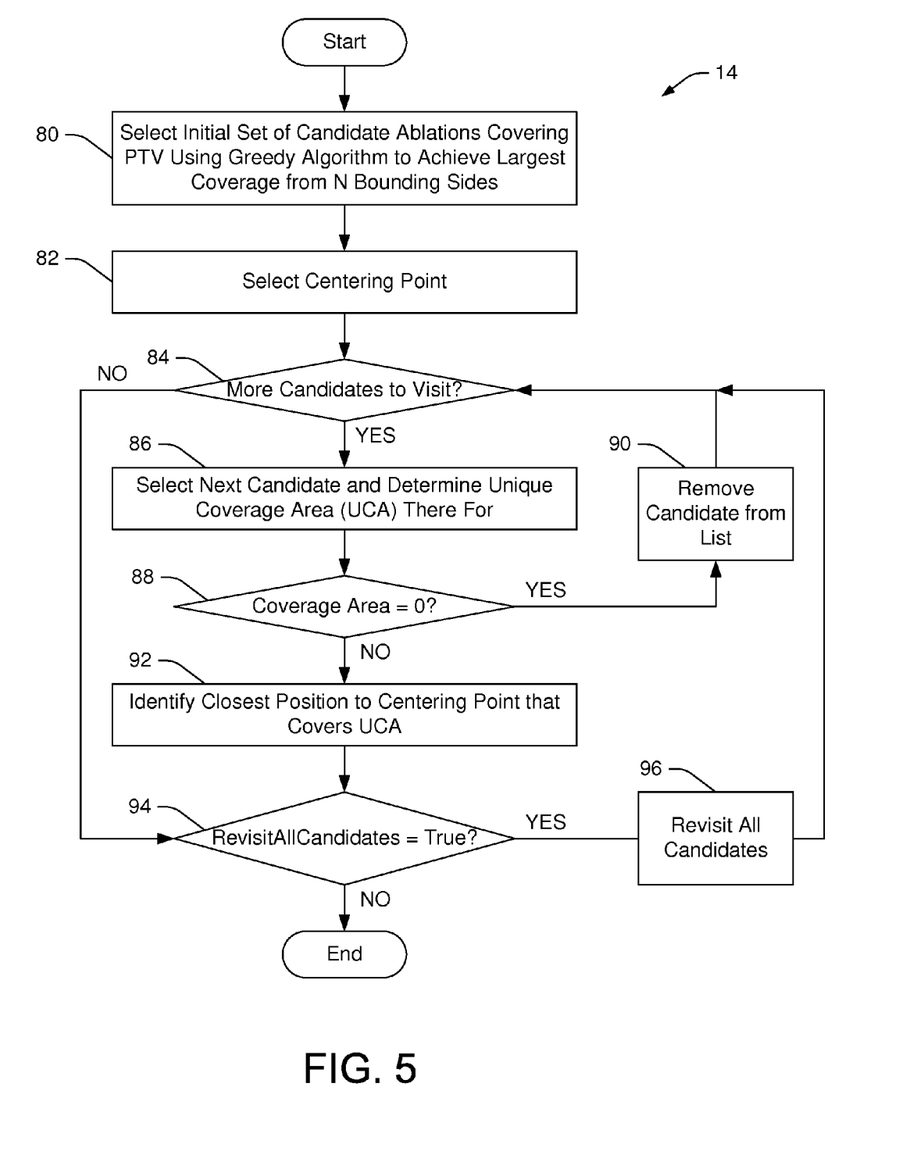
FIG. 5 illustrates a methodology for generation an ablation planning solution, in accordance with various features.

FIG. 5 illustrates a methodology that is performed by optimization component 14 for generating an ablation planning solution, as discussed herein with regard to preceding figures and in accordance with various features. At 80, the routine 28 generates an initial set of candidate ablation ellipsoids to envelope a PTV for a tumor in a patient. The set of initial candidate ablation regions is generated using a greedy algorithm to achieve maximal coverage from N bounding sides. For example, in a case where N=6, the PTV is bounded by a box or cube with six sides. However, it will be appreciated that the PTV can be bounded by any suitable polyhedron (including but not limited to tetrahedrons, octahedrons, dodecahedrons, icosahedrons, Kepler-Poinsot solids, Archimedean solids, regular polyhedrons, irregular polyhedrons, etc.) in order to further optimize ablation planning and a number of ablations performed to eradicate a tumor and/or PTV.

At 82, a centering point, or centroid, is selected for the PTV, which may be the center of mass the tissue enveloped by the PTV (e.g., tumor mass plus buffer region). At 784, a determination is made regarding whether all candidate ablation ellipsoids have been visited, or evaluated. If it is determined at 84 that all candidate ablation ellipsoids have been evaluated, then the method jumps to 94, where a determination is made regarding whether all candidate ablation ellipsoids require re-evaluation. If determination at 94 is negative, then the method terminates. If the determination at 94 is positive, then the method reverts to 84 for reiteration of candidate ablation ellipsoid evaluation.

If it is determined at 84 that one or more candidate ablation regions requires evaluation, then at 86 a subsequent candidate is selected, and a unique coverage area (UCA) there for is determined. The UCA can be viewed as an area or region of the PTV that is enveloped only, or "uniquely," by the specific candidate ellipsoid volume being evaluated. At 88, a determination is made as to whether the UCA is equal to zero. If the UCA is equal to zero, then the candidate ablation ellipsoid in question does not cover any portion of the PTV that is not already covered by another candidate volume, and is removed from the candidate list at 90. The method then reverts to 84 for a determination of whether there are any remaining candidate ablation volumes to be evaluated.

If the determination at 88 indicates that the UCA for the candidate volume is non-zero, then the candidate is valid and retained in the candidate list and the method proceeds to 92. At 92, a point is identified that represents a closest position to the centering point selected at 82 that the candidate ellipsoid center can occupy while still enveloping the UCA. It will be appreciated that the identification of the closest potential ellipsoid center position to the centering point that still permits the ellipsoid to envelop the UCA can be further constrained to ensure that the ellipsoid ablation region does not envelop a critical region, such as a bone or other area that can harm the patient if ablated.

If the ellipsoid center is not already at the identified point, then the candidate ellipsoid is moved, which triggers a re-evaluation of all candidate ellipsoids still in the candidate list. At 94, a determination is made regarding whether all candidates in the list are to be re-evaluated. If so (e.g., if one or more candidates in the candidate list was moved), then all candidates are revisited at 96, and the method reverts to 84 for further iteration and optimization of the ablation planning solution. When all candidates' centers are as close to the centering point as possible while still covering their respective UCAs, the solution has stabilized and the routine terminates.

In accordance with other features, functional data related to, for instance, tumor density and/or growth activity can be considered when planning and optimizing ablation points. For instance, if the density of the tumor is greater in one region than in another, the denser region may require more ablation than the less dense region. According to another example, a portion of the tumor exhibiting more rapid growth than the rest of the tumor may be identified and targeted for more aggressive ablation than the rest of the tumor to ensure that it is eradicated. Thus, functional data related to the tumor can be employed when optimizing an ablation plan in order to account for relative strengths and weaknesses in the tumor mass.

Still other variations include performing adaptive planning techniques during optimization, which include, without being limited to, consideration of a priori knowledge of proximity of and/or distance between a critical region and the PTV, ablation temperature and duration for a given probe as a function of functional data associated with the mass, effects of heat sinks located near the PTV (e.g., structures that will draw heat from the ablation region and thereby affect ablation of the PTV), etc.

Figure 6A:
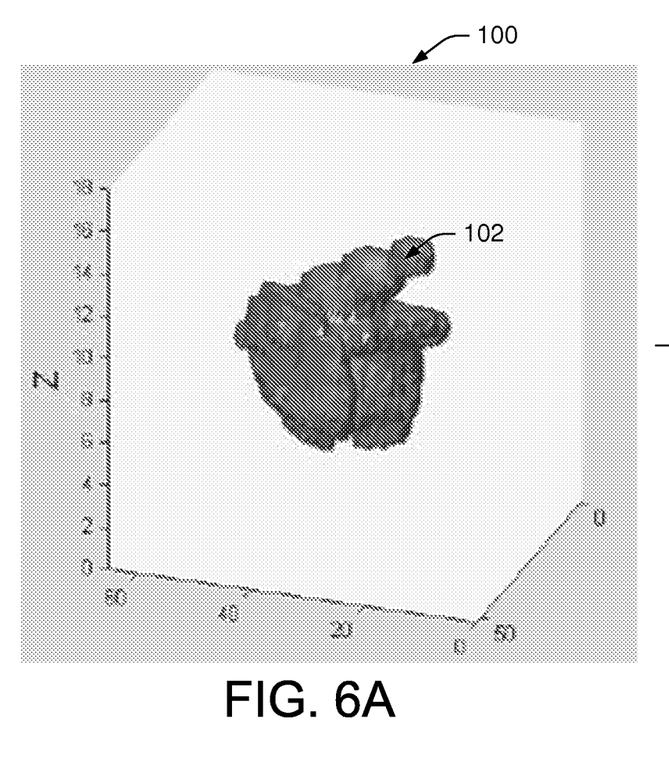
FIGS. 6A and B illustrate images that may be presented to a user via a GUI when performing various actions associated with ablation planning.

FIG. 6A image 100 illustrates a 3D segmented, irregular shape tumor with margin defining a PTV 102. The size and irregularity of the shape of the PTV poses a problem for conventional ablation procedures, since it cannot be completely covered by a single ablation of this size. Even if a sufficiently large ablation was possible, it would simultaneously cause a large amount of collateral damage, killing healthy tissue, if not ideally shaped. Since there are a finite number of ablation probes, each with fixed ablation zones, the task is to simulate each of the possibilities so that the best probe can be selected. However, as illustrated by image 106 in FIG. 6B, a plurality of ellipsoid ablation regions 108 are computed, for a given ablation probe. Determining the ellipse centers to cover the PTV 102 correlates to routine 28 of FIG. 2, described above.

Figure 6B:
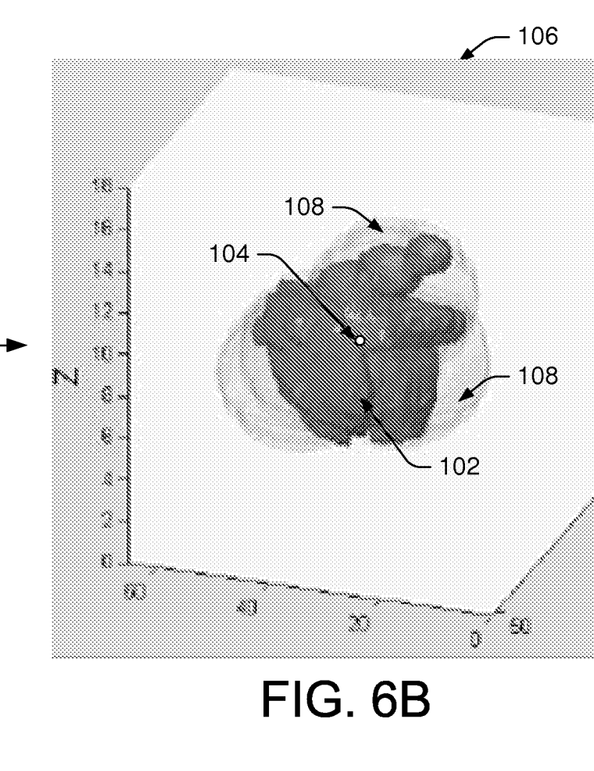

The first set of ellipses 108 is generated to cover the largest possible "bites" corresponding to the ablation volume of the PTV. In one embodiment, a bounding box or cube is defined about the PTV and a point of tangency on each of the six faces of the PTV's bounding box. The largest bite, which covers a maximum number of PTV voxels (e.g., volumetric pixels that represent a points in 3-D space), is selected from the six points, and the corresponding voxels are deleted from the PTV to be covered. This action is iteratively repeated until the PTV has no more uncovered pixels. The ellipses generated up to this point are the candidate ellipses for ablation.

A point within the PTV 102 is selected, e.g. the center of mass, called the centering point 104. Routine 28 visits each ellipse in the list of candidate ellipses in turn. For each candidate, a unique volume that the ellipse contributes to the coverage, called the Unique Coverage Area (UCA), is determined. If the UCA is zero (0), then the ellipse does not cover any unique portion of the PTV 102, which can be due to the movements of other ellipses. When this occurs, the ellipse having the null UCA is removed from the candidate list, and the next ellipse evaluated. If the ellipse has a non-zero UCA, a binary search is performed to test locations between the current ellipse center and the centering point 104 of the PTV 102 to find the location nearest to the centering point 104 where this ellipse can be moved, while still covering the UCA. Moving ellipse centers toward the centering point 104 ensures that the entire tumor mass is ablated while minimizing undesired ablation of tissue surrounding the tumor. That is, moving the ellipse centers toward the centering point 104 shrinks the PTV 102 to fit the tumor while minimizing damage to healthy tissue near the perimeter of the PTV 102. If any of the ellipses is able to be moved closer to the centering point 104 of the PTV 102 while still covering its UCA, then the positions of all candidate ellipses are re-examined. When no ellipse centers can be moved closer to the centering point 104 of the PTV 102 without compromising the coverage of their respective UCAs, the ablation planning solution has stabilized. Optionally, this process can be repeated with the initial set of covering ellipses results in a smaller number of ellipses.

Figure 8:
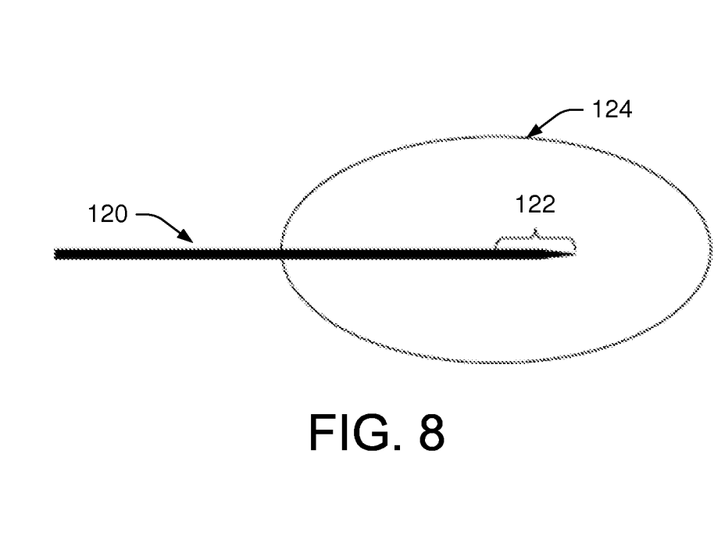
FIG. 8 illustrates an ablation probe that may be utilized to generate the ablation ellipsoids.

In FIG. 7, an image 110 of a plurality of the ellipsoid ablation volumes 108 each ellipsoid have a center 114, which is determined as described above with regard to the preceding figures, and has a known volume that is a function of the selected probe size and ablation duration. With reference to FIG. 8, an ablation pattern for an ablation probe 120 is depicted by the elliptical region 124. The ablation probe 120 is inserted into a tumor mass or PTV in a patient along a selected trajectory from an insertion point on the skin to the PTV to facilitate ablation of all or a portion of the PTV. According to an example, the target location for the probe tip is beyond the midpoint of the ellipsoid, and therefore the position of the probe tip is controlled to a distance 122 beyond the ellipse center 114 to ensure that the ablation occurs in the desired position. It will be appreciated that distance 122 typically varies from probe to probe and is not intended to be limited to the actual and/or scaled distance represented in FIG. 6.

Figure 9A:
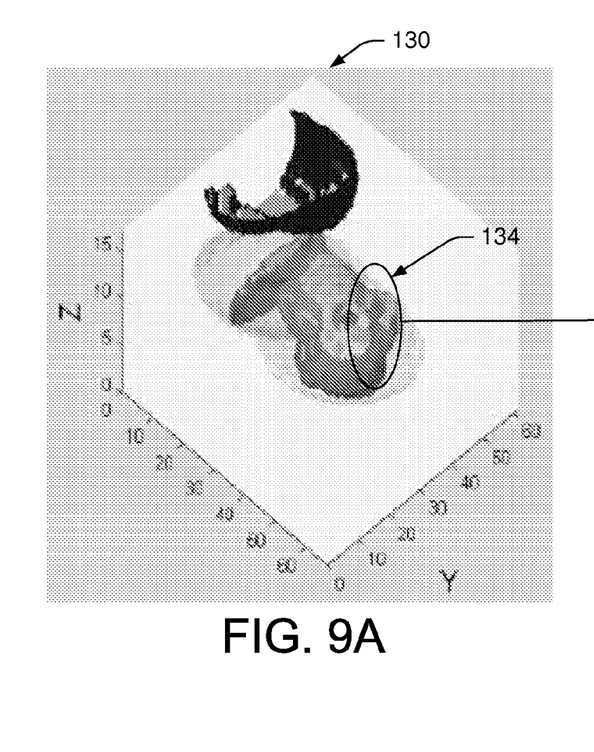
FIGS. 9A and B illustrate computer-modeled images of a planned target volume (PTV) and candidate ellipsoid ablation volumes that overlap a critical region, such as a bone.
Figure 9B:
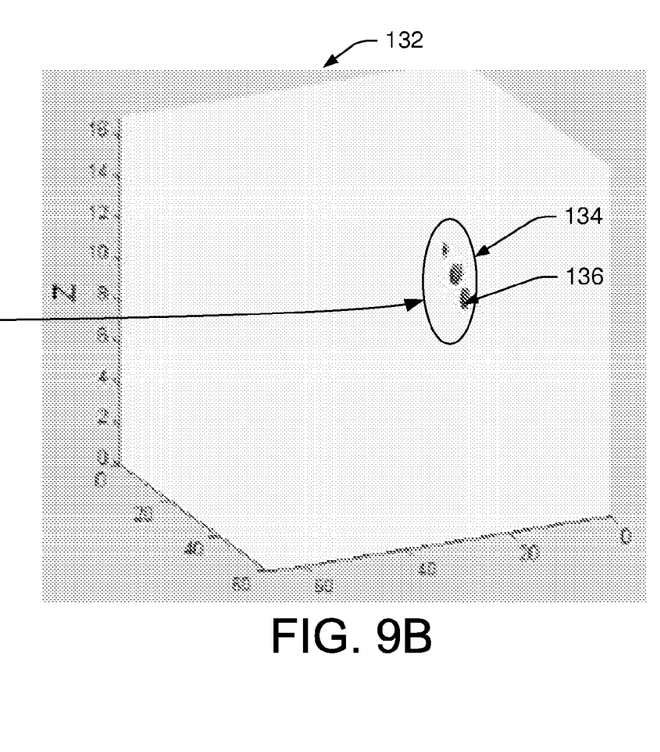

FIG. 9A illustrates computer-modeled images of a PTV and candidate ellipsoid ablation volumes that overlap a critical region 136, such as a bone. For instance, in a scenario in which the critical region is so difficult to access that, without extraordinary effort, some small portions of the tumor cannot be reached, actions are performed to ensure that the critical region 136 is not ablated while keeping a number of ablations to a minimum. In the image 130, an area 134 encompasses a plurality of areas that are that are too close to a critical region 136 to permit ablation. In image 132 (FIG. 9B), the unablatable areas are presented to a surgeon (e.g., via the GUI 18 or the like) as being highlighted so that the surgeon can take appropriate action. For example, the surgeon can select a different ablation probe. In this example, a smaller probe with a smaller ablation ellipsoid volume is selected whose ellipsoid volume does not intersect the highlighted critical volume. According to another example, the surgeon injects saline into a space between the tumor and the critical region 136 to separate the tumor from the critical region 136. If a different probe for one or more of the ablations is selected, the optimization routine 28, FIG. 2 is advantageously repeated. Similarly, if saline is injected to increase a space between the tumor and the critical region 136, the PTV is reevaluated and the optimization routine 28 is repeated to account for changes caused by the saline injection.

Figure 10:
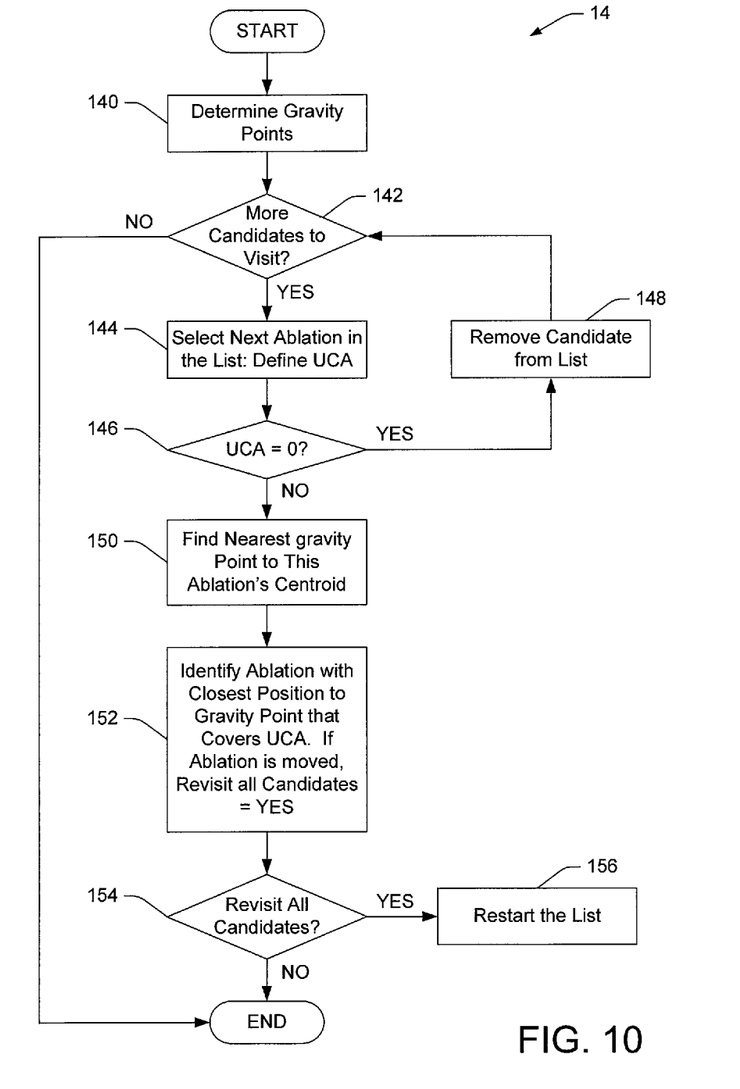
FIG. 10 illustrates a method that uses multiple gravity points to further reduce the number of ablations.

FIG. 10 illustrates a method that is performed by optimization component 14 for planning an ablation procedure, in accordance with some embodiments. The method permits ablation volumes to be pulled toward a centroid point as though by gravity, which facilitates minimizing over-ablation of tissue outside of a typical lesion, while providing the potential for overlapping regions to consolidate. The method can further reduce the number of ablation volumes by creating additional "gravity centers," or points, that further reduce the number of ellipses.

At 140, a number of "gravity points" are determined. At 142, a determination of whether there are more candidate ablation volumes to analyze is made. If there are no further candidate ablation volumes to evaluate, then the method terminates. However, if one or more other ablation volumes remain to be evaluated, then at 144 the next candidate is selected, and a UCA therefor is define and/or determined. At 146, a determination is made regarding whether the UCA is equal to zero (e.g., the candidate does not have a unique coverage area). If so, then at 148 the candidate is removed from the list and the method reverts to 142. If the candidate has a UCA, then at 150, a nearest gravity point to the candidate ablation volume's centroid is determined.

At 152, an ablation volume nearest to the gravity point while still covering the UCA is identified. If the ablation volume is moved to ensure that the UCA is still covered, then a "revisit all candidates" condition is true. At 154, a determination of whether the "revisit all candidates" condition is true is made, and if so, then the list of candidate ablation volumes is revisited in total, at 156. In this case, the method repeats. If no candidate ablation volume has been moved, then the method terminates.

The following discussion provides an example of a manner in which gravity points are determined. A "tumor-to-ablation" factor (TAfactor) can be defined as spherical tumor radius/spherical ablation radius. Thus, when TAfactor is less than or equal to 1, one ablation will cover the tumor. When 1<TAfactor<=1.25, then six ablations cover the tumor. When 1.25<TAfactor<=1.66, then 14 ablations cover the tumor, and so on. Since the method permits ablation planning for arbitrarily shaped tumors, it can be desirable to use the more general and flexible ellipsoid for the ablation shape rather than a sphere, since ablation regions are often ellipses, but can also be spheres (an ellipse with equal a,b,c axes). The following example, for simplicity, describes the procedure with two different sized spheres for the tumor and ablation.

An important difference between this method and the method of FIG. 5 is the identification of "gravity points,"

which pull the ablations from the center toward a collection of regional nodes, where they can be further aggregated to minimize the number of ablations. The gravity points for a set of 6 spheres (1<TAfactor<=1.25) are located, for example, at a distance Q of 0.76*ablation-radius from the center of the tumor along each of the X, Y and Z axes (in both + and − directions). For example, if the tumor has a radius of 2.5, and the ablation has a radius of 2, then the TAfactor is exactly 1.25. The locations of the gravity points are therefore Q=0.76*2=1.52 away from the center of the tumor along each of the 3 axes. If the tumor were centered at (0,0,0), then the gravity points would be located at: (0,0, 1.52), (0,0,−1.52), (0, 1.52,0), (0,−1.52,0), (1.52,0, 0), (−1.52,0,0).

The gravity points for a set of 14 spheres (1.25<TAfactor<=1.66) are a combination of 6 spheres located along the x,y,z axes and 8 more that fill the 'corners' between them. The first 6 are at a farther distance W=0.90*ablation-radius, from the center of the tumor. For example, if the Tumor has a radius of 3.32, and the ablation has a radius of 2, then the TAfactor is exactly 1.66. Calculated similarly, the first 6 are located W=0.9*a=1.8 from the center of the 3.32 radius tumor. The remaining 8 gravity points are at the diagonals. These are formed by equal, absolute distances along two different axes. The absolute distance $L=W^2 \sqrt{1/2}$. In this example, $L=(1.8)^2 \sqrt{1/2}=3.24*0.07071=2.291$. The diagonals are located at the following locations for a sphere: (L,L,L), (L,L,−L), (L,−L,L), (L,−L,−L), (−L,L,L), (−L,L,−L), (−L,−L,L), (−L,−L,−L). Where (1.25<TAfactor<=1.66), the first consolidation can be performed to draw the ablation centers toward the very center, as described above, and then the steps of FIG. 10 can be executed to draw them toward the nearest of the gravity points.

This technique can be used advantageously if the tumor is circumscribed by a sphere, thus making it somewhat more general, and when the ablation probe generates a spherical ablation volume. The technique can also be used when the TAfactor is >1.66. This is especially true when the tumor is circumscribed by a sphere, and the current practical limit for number of ablations is limited not only by the 15 minutes required per ablation, but also in the accuracy of placement. As ablation techniques become faster, probe placement can be guided with imaging or tracking to improve accuracy.

In practice, the tumor can be an arbitrary shape and the ablation shape can be arbitrary. In these situations, the gravity points can be determined by inscribing the tumor in a sphere and inscribing the ablation in a sphere. The ratios of the radii can be used to define the TAfactor and to calculate gravity points. This simplicity enables the technique to compute quickly, while adapting to arbitrary shaped tumors and ablations. A quick computation then allows multiple scenarios to be evaluated, so that entry points with the fewest ablations, and/or the least collateral damage, can be identified.

Alternatively, more sophisticated computations can be used to define gravity points where the PTV is enclosed by a sphere, and the elliptical ablations are calculated to cover the sphere. The centroids of possibly many ellipses that cover the sphere are the gravity points.

According to another embodiment, step 80 from FIG. 5 can be performed to create the initial ablations, and can be followed by the steps of FIG. 10. This technique can be effective in a large number of cases, however in other cases it is preferable to perform both the steps of FIG. 5 and then the steps of FIG. 10. For example, for spiculated (spiked) lesions, characteristic of some breast cancers and others, condensing the coverage to the center and then re-distributing it, can reduce the overall number of ablations.

Having thus described the preferred embodiments, the invention is now claimed to be:

1. A system for planning an ablation procedure for ablation of a tissue mass in a patient, including:
   a graphical user interface that presents a representation of the mass to a user; and
   an optimization component configured to:
   receive image data related to the mass;
   determine one or more ablation regions to cover the mass; and
   determine a unique coverage area (UCA) for each of a predetermined number of candidate ablation regions such that the UCA for a given candidate ablation region includes a portion of a planned target volume (PTV) that is covered solely by the given candidate ablation region;
   wherein the optimization component is further configured to generate an initial list of the candidate ablation regions, each having a characteristic point at which a probe associated with an ablation component is positioned to treat a portion of the mass in each ablation region;
   wherein the optimization component is further configured to generate the initial list of the candidate ablation regions to achieve maximal coverage of the PTV from a point of tangency on each of N bounding sides that encompass the PTV.

2. The system according to claim 1, wherein the optimization component is configured to generate the planned target volume (PTV), which includes the mass.

3. The system according to claim 1, wherein the optimization component is configured to remove a candidate ablation region from the list of candidate ablation regions if the candidate ablation region does not have a UCA.

4. The system according to claim 1, wherein the optimization component is configured to utilize a ray marching technique to generate at least one candidate insertion point on the skin of the patient, through which the probe associated with the ablation component is inserted along a trajectory to the PTV while avoiding one or more critical regions.

5. The system according to claim 1, wherein the optimization component is configured to optimize an ablation plan as a function of at least one of functional data associated with the mass, location of one or more heat sinks near the mass, a shape of the probe associated with the ablation component, a size of the probe associated with the ablation component, and a number of different ablation probes utilized during ablation.

6. The system according to claim 1, wherein the optimization component is configured to optimize an ablation plan as a function of at least one of entry angles of the probe associated with the ablation component, ablation temperature, ablation time, and critical regions.

7. The system according to claim 1, wherein the optimization component is configured to utilize prior knowledge of at least one of a proximity of the PTV to a critical region, an ablation time associated with the probe associated with the ablation component, an ablation temperature associated with the probe associated with the ablation component, and one or more heat sinks located near the PTV.

8. The system according to claim 1, wherein the optimum number of ablation regions is a minimum number of ablation regions that covers the mass.

9. The system according to claim 1, wherein the optimization component is configured to receive information describing the planned target volume (PTV), which encompasses the mass, the information comprising outlined boundaries on one or more different views of the representation of the mass, and wherein the optimization component is configured to generate 3D voxels representing the planned target volume.

10. The system according to claim 1, wherein N equals six.

11. The system according to claim 1, wherein the N bounding sides form a tetrahedron.

12. The system according to claim 1, wherein the N bounding sides form an octahedron.

13. The system according to claim 1, wherein the N bounding sides form a dodecahedron.

14. The system according to claim 1, wherein the N bounding sides form an icosahedron.

15. The system according to claim 1, wherein the N bounding sides form a Kepler-Poinsot solid.

16. The system according to claim 1, wherein the N bounding sides form a Archimedean solid.

17. The system according to claim 1, wherein the N bounding sides form a regular polyhedron.

18. The system according to claim 1, wherein the N bounding sides form an irregular polyhedron.

19. A system for planning an ablation procedure for ablation of a tissue mass in a patient, including:
   a graphical user interface that presents a representation of the mass to a user; and
   an optimization component configured to:
   receive image data related to the mass;
   determine one or more ablation regions to cover the mass; and
   determine a unique coverage area (UCA) for each of a predetermined number of candidate ablation regions such that the UCA for a given candidate ablation region includes a portion of a planned target volume (PTV) that is covered solely by the given candidate ablation region;
   wherein the optimization component is configured to generate the planned target volume (PTV), which includes the mass;
   wherein the optimization component is configured to generate an initial list of candidate ablation regions, each having a characteristic point at which a probe associated with an ablation component is positioned to treat a portion of the mass in each ablation region;
   wherein the optimization component is configured to execute a binary search algorithm to determine whether the characteristic points of the given candidate ablation region can be moved closer to a centering point of the PTV without compromising coverage of the UCA of the given candidate ablation region.

20. The system according to claim 19, wherein the optimization component is configured to continue optimizing a model for tumor mass ablation until no candidate ablation region can be moved closer to the centering point and all UCAs are covered.

21. A system for planning an ablation procedure for ablation of a tissue mass in a patient, including:
   a graphical user interface that presents a representation of the mass to a user; and
   an optimization component configured to:
   receive image data related to the mass; and
   determine one or more ablation regions to cover the mass;
   wherein the optimization component includes:
   a routine that selects an initial set of candidate ablation regions that cover a planned target volume (PTV);
   a routine that selects a centering point of the PTV;
   a routine that determines whether one or more candidate ablation regions in the initial set of candidate ablation regions remain to be evaluated;
   a routine that selects a candidate ablation region and evaluates a unique coverage area (UCA) there for;
   a routine that determines whether the UCA for the candidate ablation region is equal to zero;
   a routine that removes the candidate ablation region from the initial set of candidate ablation regions if the UCA is equal to zero;
   a routine that identifies a closest position to the centering point, to which the candidate ablation region is moved, while still covering the UCA, if the UCA is not equal to zero;
   a routine that determines that all candidate ablation regions are ready for reevaluation if one or more candidate ablation regions has been moved closer to the centering point; and
   a routine that causes all candidate ablation regions to be reevaluated.

22. A system that facilitates planning a tumor ablation procedure to eradicate a tumor in a patient, including:
   a processor configured to execute computer-readable instructions stored on a non-transitory computer-readable medium, the instructions comprising:
   generating an image of a tumor mass in a patient;
   receiving information related to the tumor mass and information related to removal of the tumor mass;
   generating a plurality of volumes that envelop a planned target volume (PTV) for ablation, wherein the PTV includes the tumor mass;
   optimizing placement of the volumes by identifying an optimum number of volumes to cover the entire PTV;
   for each volume, identifying a unique coverage area (UCA) that covers a unique portion of the PTV; and
   generating an initial list of candidate volumes, each having a characteristic point at which a probe associated with an ablation component is positioned to treat a portion of the tumor mass;
   wherein the generating of the initial list of the candidate volumes generates the initial list of the candidate volumes to achieve maximal coverage of the PTV from a point of tangency on each of N bounding sides that encompass the PTV.

23. The system according to claim 22, wherein the instructions further comprise optimizing an ablation plan as a function of functional data associated with the mass.

24. The system according to claim 22, wherein the instructions further comprise optimizing an ablation plan as a function of location of one or more heat sinks near the mass.

25. The system according to claim 24, wherein the heat sink is an aorta.

26. The system according to claim 22, wherein the instructions further comprise optimizing an ablation plan as a function of a shape of the probe associated with the ablation component.

27. The system according to claim 22, wherein the instructions further comprise optimizing an ablation plan as a function of a size of the probe associated with the ablation component.

28. The system according to claim 22, wherein the instructions further comprise optimizing an ablation plan as a function of a number of different ablation probes utilized during ablation.

29. The system according to claim 22, wherein the instructions further comprise optimizing an ablation plan as a function of entry angles of the probe associated with the ablation component.

30. The system according to claim 22, wherein the instructions further comprise optimizing an ablation plan as a function of ablation temperature, ablation time, and critical regions.

* * * * *